United States Patent [19]

Zuckerman

[11] Patent Number: 4,739,120

[45] Date of Patent: Apr. 19, 1988

[54] PROCESS FOR THE HYDROGENATION OF NITRILES TO PRIMARY AMINES

[75] Inventor: Marie F. Zuckerman, North Haven, Conn.

[73] Assignee: The Dow Chemical Company, Midland, Mich.

[21] Appl. No.: 898,662

[22] Filed: Aug. 21, 1986

[51] Int. Cl.$^4$ ............................................. C07C 85/12
[52] U.S. Cl. .................................... 564/385; 564/415; 564/448; 564/490; 564/491; 564/492; 564/493
[58] Field of Search ............... 564/385, 415, 448, 490, 564/491, 492, 493

[56] References Cited

U.S. PATENT DOCUMENTS

| | | | |
|---|---|---|---|
| 2,287,219 | 6/1942 | Young et al. | 260/583 |
| 2,449,036 | 9/1948 | Greenfeld | 260/583 |
| 3,253,040 | 5/1966 | Potter et al. | 564/448 |
| 3,372,195 | 3/1968 | Little | 260/570.7 |
| 3,565,957 | 2/1971 | Mirviss et al. | 260/583 |
| 3,821,305 | 6/1974 | Bartalini et al. | 564/490 |
| 3,998,881 | 12/1976 | Butte et al. | 260/563 R |
| 4,186,146 | 1/1980 | Butte et al. | 260/570.5 P |
| 4,235,821 | 11/1980 | Butte et al. | 564/491 |
| 4,254,059 | 3/1981 | Grey et al. | 564/492 |

FOREIGN PATENT DOCUMENTS

| | | | |
|---|---|---|---|
| 703463 | 2/1965 | Canada | 564/490 |
| 19893 | 12/1980 | European Pat. Off. | |

OTHER PUBLICATIONS

"Catalytic Hydrogenation in Organic Synthesis" by P. N. Rylander (1979), pp. 138 to 152, Academic Press, New York, N.Y.

Primary Examiner—Glennon H. Hollrah
Assistant Examiner—John A. Sopp

[57] ABSTRACT

An improved process is disclosed for the catalytic hydrogenation of an organic nitrile group containing compound to a primary aminomethyl group in the presence of a rhodium catalyst, a basic substance, and in a two-phase solvent system comprising an immiscible organic solvent and water.

15 Claims, No Drawings

PROCESS FOR THE HYDROGENATION OF NITRILES TO PRIMARY AMINES

FIELD OF THE INVENTION

This invention relates to a process for obtaining compounds containing at least one aminomethyl group and is more particularly concerned with an improved process for hydrogenating organic nitrile groups to the corresponding primary aminomethyl groups.

DESCRIPTION OF THE PRIOR ART

The catalytic hydrogenation of nitrile groups to the reduced form of primary aminomethyl groups is a very well known and documented procedure. A majority of the catalytic reductions have been carried out at elevated pressures (i.e. 600 to 2500 psig) and elevated temperatures (i.e. 100° to 180° C.); see, for example, "Catalytic Hydrogenation in Organic Synthesis", by Paul N. Rylander (1979), pp. 138 to 152, Academic Press, New York, N.Y. One of the problems plaguing the hydrogenation, aside from reaching high conversions, is the formation of unwanted secondary and tertiary amines. Certain techniques have been employed in the art to reduce such side-product formation including the use of ammonia in the reduction. As an extension of the ammonia method, the use of basic materials such as sodium hydroxide and sodium methoxide have been employed as promoters. Furthermore, the use of a wide variety of solvents have been investigated ranging from water to a broad class of organic solvents and even mixtures of solvents. Typical of such prior art is the following.

U.S. Pat. No. 2,287,219 discloses the hydrogenation of cotton seed fatty acid nitriles to the primary amines using Raney nickel and an aqueous solution of alkaline reacting materials, i.e. ammonia and/or caustic soda. U.S. Pat. No. 2,449,036 teaches the hydrogenation of nitriles to primary amines using nickel or cobalt catalysts without the need for ammonia provided the reduction is in the presence of a strong aqueous basic solution in ethyl alcohol. U.S. Pat. No. 3,372,195 discloses the ruthenium catalyzed reduction of nitriles using a broad assortment of solvent classes including water, alcohols, ethers, tertiary amines, and amides. Rhodium catalyzed reduction of nitrilotriacetonitrile to tris(2-aminoethyl)amine in ethanol and ammonia is taught in U.S. Pat. No. 3,565,957. Rhodium is employed to catalyze the reduction of both the nitriles and the benzene ring when iso- or terephthalonitrile is hydrogenated in solvents such as ethers, alcohols and chloroform using ammonia as taught in U.S. Pat. No. 3,998,881. U.S. Pat. No. 4,186,146 discloses the hydrogenation of aromatic nitriles to the corresponding aminomethylbenzene derivatives in a solvent system containing water, ammonia, and water miscible ether solvents using a cobalt or nickel catalyst. Likewise, U.S. Pat. No. 4,235,821 discloses the hydrogenation of aliphatic nitriles in a solvent system of water, ammonia, and water miscible ethers but using a ruthenium catalyst.

Ammonia is avoided in U.S. Pat. No. 4,254,059 in the hydrogenation of nitriles at low temperatures and pressures in a wide variety of solvents. However, the catalysts called for belong to a rather exotic class of organoligand additives of anionic hydride compositions based on Group VIII metals.

European patent application No. 19893 describes the hydrogenation of 1,3,5-tricyanobenzene to 1,3,5-tris-(aminomethyl)cyclohexane either directly in one step or as a two-step process of a first hydrogenation to the 1,3,5-tris(aminomethyl)benzene followed by the second hydrogenation of the benzene ring to the final product. The hydrogenation conditions disclosed are very broad including most of the known, or, at least readily available, catalysts such as the platinum metal group (platinum, ruthenium, and rhodium) as well as Raney nickel and Raney cobalt. Solvent classes disclosed are also broad including aromatic hydrocarbons, alcohols, ethers, water, liquid ammonia, and basic substances like sodium hydroxide, and the like. However, the preferred solvents are alcohols, or alcohol-water, or alcohol-aromatic hydrocarbons. Hydrogen pressures and reaction temperatures are both relatively high and the use of ammonia is particularly recommended.

It has now been discovered that when the rhodium catalyzed hydrogenation of a nitrile is carried out in the presence of a basic substance and in a two-phase solvent system, high conversion and high selectivity to the primary aminomethyl group are obtained.

Additionally, the present method eliminates the need for ammonia, and, at the same time, provides the high yield of desired product at surprisingly low temperatures and low hydrogen pressures.

SUMMARY OF THE INVENTION

This invention comprises an improved process for the catalytic hydrogenation of an organic nitrile group containing compound to a primary aminomethyl group in the presence of a rhodium catalyst, a basic substance, and a solvent wherein the improvement comprises employing a two-phase solvent system comprising an immiscible organic solvent and water.

The term "organic nitrile group containing compound" means an organic compound containing at least one —CN group attached to a residue selected from the group consisting of aromatic, cycloaliphatic and aliphatic residues.

The term "basic substance" means a basic organic or inorganic material having a pH of at least 8 as measured in aqueous solution.

DETAILED DESCRIPTION OF THE INVENTION

In carrying out the process of the present invention the procedures commonly used in the art to carry out catalytic hydrogenations are employed. That is to say, the hydrogenation of the nitrile group to the aminomethyl group is carried out in an autoclave, or analogous vessel designed to retain a multiphase system under conditions of elevated temperatures and pressures of hydrogen. In this regard, the U.S. patents cited supra provide various catalytic hydrogenation apparatuses and methods which can be employed in the present process, and, to this extent, the disclosures of U.S. Pat. Nos. 2,287,219, 2,449,036, 3,372,195, 3,565,957, 3,998,881, 4,186,146, 4,235,821, and 4,254,059 are incorporated herein by reference.

The novel feature of the present process resides in the employment of a two-phase solvent system for the hydrogenation which system comprises an aqueous phase and an immiscible organic solvent phase. The prior art has disclosed the use of water and various organic solvents, and even mixtures of water with miscible solvents such as ethyl alcohol, dioxane, tetrahydrofuran, and the like. However, to the best of my knowledge, the unexpected benefits to be gained by hydrogenating a nitrile group in a two-phase system combining water with an insoluble organic solvent have not been recognized heretofore.

Any organic solvent which is relatively immiscible with water can be employed. The term "relatively immiscible" means less than 1 g. is soluble in 100 g. of water at about 20° C. Included in this class of organic solvents are the aromatic hydrocarbons having 6 to 12 carbon atoms, inclusive; the alicyclic hydrocarbons having 5 to 10 carbon atoms, inclusive; the alkanes having 6 to 12 carbon atoms, inclusive, and isomeric forms thereof; and the above classes of solvents substituted by inert substituents. This latter term means any radical which does not itself react with hydrogen or otherwise interfere with the hydrogenation of the nitrile, and is inclusive of lower-alkyl having 1 to 8 carbon atoms, inclusive, such as methyl, ethyl, propyl, butyl, amyl, hexyl, heptyl, and isomeric forms thereof; halo, i.e. chloro, bromo, fluoro, and iodo; lower-alkoxy, i.e. alkoxy from 1 to 8 carbon atoms, inclusive, such as methoxy, ethoxy, propoxy, butoxy, pentyloxy, hexyloxy, heptyloxy, octyloxy, and the like, including isomeric forms thereof. It will be readily apparent that when the inert substituent is lower-alkyl this would be in connection with the aromatic or alicyclic hydrocarbon classes of solvents only since the class of alkane solvents already includes isomeric forms thereby inherently including lower-alkyl substituents.

Illustrative of organic solvents useful in the present process but not limiting thereof are benzene, toluene, xylenes, tetralin, mesitylene, durene, chlorobenzene, dichlorobenzene, bromobenzene, dibromobenzene, anisole, ethoxybenzene, butoxybenzene, and the like; cyclopentane, cyclohexane, cycloheputane, cyclooctane, methylcyclopentane, ethylcyclopentane, butylcyclopentane, 1,2-dimethylcyclopentane, methylcyclohexane, 1,4-dimethylcyclohexane, methylcycloheptane, 1,3-dimethylcycloheptane, 1,3-diethylcycloheptane, 1-methylcyclooctane, 1,4-dimethylcyclooctane, 1,5-dimethylcyclooctane, the naphthene class of hydrocarbons including typically 1,1-dimethylcyclopentane, 1,3-dimethylcyclopentane, ethylcyclohexane, and 1,2,4-trimethylcyclohexane, and the like; hexane, heptane, octane, nonane, decane, undecane, dodecane, 2,2-dimethylbutane, 3-methylheptane, 2,3-dimethylhexane, 2,2,4-trimethylpentane, 2,2,3-trimethylpentane, 2,7-dimethyloctane, 3,4-diethylhexane, and the like.

Preferred classes of solvents are the aromatic and alicyclic hydrocarbons. It will be recognized by one skilled in the art that rhodium is capable of catalyzing the hydrogenation of aromatic ring compounds to the saturated state particularly under more stringent reaction conditions such as high hydrogen pressures and high temperatures. Accordingly, the alicyclic hydrocarbons are the most preferred class of organic solvents for use in the present method, particularly when operating at higher conditions of temperature and pressure.

The amount of water or aqueous phase is not critical per se provided there is sufficient water to result in phase separation from the organic solvent. Advantageously, the water is employed in at least 3 percent by volume of the organic phase, preferably at least 5 percent. The maximum amount of water which can be employed is limited only by practical considerations such as reactor size limitations and ease of handling. Generally speaking, the proportion of water or aqueous phase can fall within a range of from about 3 to about 100 percent by volume of the organic phase, preferably from about 5 to about 60 percent.

Although not limited thereto, in one particular embodiment of the present process, the basic substance defined above is dissolved in the aqueous phase either by charging it to the reactor along with the other components including water or by predissolving it in the water to be added as an aqueous solution.

Any basic substance meeting the above definition can be employed. Typical classes of such substances are the alkali metal hydroxides, alkali metal alkoxides, alkaline earth metal hydroxides, and quaternary ammonium hydroxides having the formula $R_4N^\ominus OH^\oplus$ wherein R is independently selected from the group consisting of alkyl of 1 to 18 carbon atoms, and aryl of 6 to 10 carbon atoms. Illustrative but not limiting thereof of such substances are sodium hydroxide, potassium hydroxide, lithium hydroxide, sodium methoxide, sodium ethoxide, sodium butoxide, potassium methoxide, potassium ethoxide, calcium and barium hydroxides, tetramethyl ammonium hydroxide, tetraethyl ammonium hydroxide, tetrabutyl ammonium hydroxide, diphenyldimethyl ammonium hydroxide, tetraphenyl ammonium hydroxide, and the like.

A preferred class includes the alkali metal hydroxides with sodium hydroxide being most preferred.

In respect of the concentration of the basic substance it can be employed within a broad range of proportions and still give rise to the present improved process. However, it must be present to some degree otherwise the reduction process is seriously impeded. Within the volume proportions for the water described above, the basic substance is advantageously employed within a range of from about 0.1 molar to about 15 molar, preferably, within a range of from about 0.5 to about 5 molar and, most preferably, from about 1 to about 3 molar in the aqueous phase.

A surprising feature of the present method is the low temperature at which the nitrile groups can be reduced while still maintaining high conversions with very high selectivity to the desired aminomethyl products. While any elevated temperature may be employed including the prior art ranges up to 200° C., the hydrogenation is advantageously conducted at a temperature within the range of from about 20° C. to about 110° C., preferably from about 40° to 90° C., most preferably from about 60° to 80° C. The exact choice of temperature in any given instance is a function of the type of nitrile, specific catalyst activity, hydrogen pressure and the like. Generally speaking, the higher the hydrogen pressure, the lower the temperature required.

Another of the unexpected features of the present method is the low hydrogen pressure which can be employed. Similarly, as with temperature noted above, the prior art high pressures may be employed but in most cases will not result in any benefit over the present advantageous pressure of from about 15 to about 200 psig, and, preferably from about 30 to about 90 psig.

The catalyst employed is one containing elemental rhodium. The metal may be unsupported but is preferably supported on any of the carriers conventionally employed for this purpose in preparing hydrogenation catalysts. For example, the rhodium can be supported on alumina, carbon, kieselguhr, bentonite, asbestos, silica gel, zirconium oxide, and the like. The preferred carriers are alumina and carbon with the latter being the most preferred. The exact proportions in which the elemental rhodium is present on the carrier is not a critical factor and such ranges are usually determined by the manufacturers of such speciality items. Generally speaking, the rhodium can vary from about 0.05 to about 40 percent by weight based on rhodium and carrier weight, but is preferably within the range of about 0.5 to about 20, and, most preferably, from about 2 to about 10 percent by weight.

The proportions of catalyst employed expressed as the pure metal in respect of the nitrile group to be reduced will advantageously fall within the range of from about 0.05 to about 30 mole percent of rhodium per equivalent of nitrile. Preferably, the range is about 1 to about 10 mole percent. The term "equivalent of nitrile" means the nitrile equivalent weight which is obtained by dividing the molecular weight of the nitrile containing compound by the number of nitrile groups per mole. That is to say, that amount equivalent to one CN group would be expressed as one equivalent.

The organic nitrile group containing compounds which are hydrogenated in accordance with the present invention are any of the known (I) aromatic, (II) cycloaliphatic, or (III) aliphatic nitrile compounds as broadly defined above. By way of further definition the nitriles can be considered as falling within the formula $R'(Y)_n$ wherein Y represents the radical —CN or —XCH$_2$CH$_2$CN wherein X represents —O— or —NH— and n=an integer from 1 to 6, inclusive, provided that in the case of group (I) Y is one or more cyano groups connected directly to an aromatic residue (R') having 6 to 14 carbon atoms, inclusive; in the case of group (II) Y is one or more cyano groups connected directly to a cycloaliphatic residue (R') having 4 to 8 carbon atoms; and in the case of group (III), Y is (i) one or more cyano groups attached directly to an aliphatic residue (R') having 1 to 18 carbon atoms or (ii) one or more —XCH$_2$CH$_2$CN groups attached to the residues (R') after removal of hydroxyl groups from an organic alcohol, diol, triol, tetrol, pentol, or hexol (when X is —O—) or (R') after removal of amine groups from an organic amine, diamine, triamine, tetramine, pentamine, or hexamine (when X is —NH—) and wherein said precursor alcohols and amines have a molecular weight of from about 30 to about 10,000.

Illustrative of the nitriles but not limiting thereof are the following:

(I) Benzonitrile, o-, m-, or p-tolunitrile, o-, m-, or p-aminobenzonitrile, phthalonitrile, isophthalonitrile, terephthalonitrile, trimesonitrile, 1-naphthonitrile, 2-naphthonitile, and the like.

(II) Cyclobutanecarbonitrile, cyclopentanecarbonitrile, cyclohexanecarbonitrile, 1,4-cyclohexanedicarbonitrile, 1,2,4,5-cyclohexanetetracarbonitrile, cycloheptanecarbonitrile, 3-methylcycloheptanecarbonitrile, cyclooctanecarbonitrile, and the like.

(IIIi) Acetonitrile, propionitrile, butyronitrile, valeronitrile, capronitrile, 2,2-dimethylpropanenitrile, enanthonitrile, caprylnitrile, pelargonitrile, caprinitrile, hendecanenitrile, lauronitrile, tridecanenitrile, myristonitrile, pentadecanenitrile, palmitonitrile, margaroninitrile, stearonitrile, phenylacetonitrile, malononitrile, succinonitrile, glutaronitrile, adiponitrile, 1,3,5-tricyanopentane, and the like.

(IIIii) It will be readily apparent to one skilled in the art that this class of nitrile compounds includes the well known cyanoethylated products derived from various alcohols, polyols, amines, and polyamines as described in U.S. Pat. No. 4,235,821 cited supra whose disclosure relative thereto is incorporated herein by reference, and, U.S. Pat. Nos. 2,401,607, 3,044,989, 3,306,809, 3,372,195 and 3,436,359 whose disclosures relative thereto are also incorporated herein by reference, and additionally reference is made to the cyanoethylated products disclosed in British Patent No. 988,632. Illustratively, this includes the cyanoethylated products derived from methanol, ethanol, butanol, pentanol, and the like; from methyl amine, ethyl amine, butyl amine, octyl amine, and the like; from ethylene glycol, propylene glycol, butylene glycol, propylene glycol, diethylene glycol, dipropylene glycol, hydroquinone, phloroglucinol, 1,4-cyclohexanediol, 1,4-di(hydroxymethyl)cyclohexane, polyethylene glycols of molecular weight from 200 to 1,000, polypropylene glycols of molecular weight from 200 to 1,000, and the like; from polyols having a functionality of 2 to 6 and a molecular weight from 1,500 to 10,000 such as polyoxyalkylene polyethers, polyester polyols, polyol adducts derived from ethylene and/or propylene oxide and methylenedianiline and polymethylene polyphenylamine mixtures, vinyl reinforced polyether polyols, e.g. polyols obtained by the polymerization of styrene or acrylonitrile in the presence of the polyether, polyacetals from glycols such as diethylene glycol and formaldehyde, polycarbonate polyols such as from butanediol and diaryl carbonates, resole polyols, hydroxy terminated polybutadiene resins, and the like; from ethylene diamine, butylene diamine, polyamines of functionality from 2 to 6 such as the primary amine terminated polyether resins having molecular weights from about 600 to about 8,000 as typically disclosed in U.S. Pat. No. 3,654,370, and the like.

It will be noted that because of the tendency for rhodium to catalyze aromatic ring reduction, it is preferable that the nitrile group(s) to be reduced not be attached to an aromatic ring unless it is also desired to hydrogenate the aromatic nucleus.

A preferred class of nitrile group containing compounds for hydrogenation in accordance with the present invention are those falling within group (III), that is to say, those compounds having at least one aliphatic type nitrile group. Most preferred are those falling within the (IIIii) class wherein X = —O— said n=about 2 to about 4 which are the cyanoethylated products derived from organic polyols having about 2 to about 4 hydroxyl groups described above.

Generally speaking, the nitrile compound is soluble in the organic phase and can be either predissolved in the solvent prior to charging to the hydrogenation apparatus or it can be added separately along with the solvent. The proportions of nitrile compound relative to the amount of solvent is not a limiting factor. Optimum concentrations are often related to the type and molecular weight of the nitrile compound. Advantageously, its concentration can be from about 2 to about 30 percent by weight in said organic phase, preferably from about 5 to about 20 percent.

The progress of the hydrogenation is readily followed by observation of the amount of hydrogen uptake. Accordingly, reaction is terminated at the point at which the theoretical quantity of hydrogen has been absorbed. The time will vary depending on the number and type of nitrile groups, hydrogen pressure, and temperature, and, to some extent, the solvent employed. One of the advantages inherent in the present method is the short hydrogenation times which, in some cases, can be as low as 2 hours or less.

The catalyst is separated from the reaction mixture using conventional filtration procedures such as suction filtration. The use of filter aids such as Celite is oftentimes helpful. The catalyst is readily recoverable for direct recycle or subjected to a thermal recovery step prior to recycle.

Separation of the organic phase from the aqueous phase is easily carried out. Generally speaking, the majority, if not all, of the reduced amine product will be in the organic layer. This is true particularly of high molecular weight polyamine materials. In the event that low molecular weight amine products are involved, then there will be some product partition which will necessitate product recovery from the water layer using conventional solvent extraction methods, evaporation, salting-out, and the like.

The separated organic phase is optionally dried to remove traces of water. Solvent is then removed using conventional distillation methods to provide the product either as a solid or liquid. The products can be purified, if necessary, or if desired, using conventional methods of recrystallization, solvent extraction, steam distillation, and the like. Generally speaking, when the products are derived from the hydrogenation of the cyanoethylated high molecular weight polyols or polyamines, they are in the form of viscous oils. In this connection, it is not always possible, nor indeed even necessary, to obtain the products in absolutely pure form. Quite often the cyanoethylated starting material contains unreacted polyol or polyamine which results in hydrogenated product mixtures containing minor proportions of polyol or polyamine.

The amines produced in accordance with this invention find utility in a broad area of applications such as chemical intermediates, catalysts for polyurethane formation, extenders in polyurethane formation, crosslinking agents and curatives for epoxies, and the like.

The following examples describe representative specific embodiments of the present invention and set forth the best mode contemplated by the inventor of carrying out the invention but are not to be construed as limiting.

EXAMPLE 1

A 250 ml. borosilicate glass Parr reaction bottle was charged with 2.22 g. (0.01 mole) of 1,4-bis($\beta$-cyanoethoxy)butane, 30 ml. of toluene, 421 mg. of 5 percent rhodium/carbon supported catalyst (Engelhard sample #11953-28-D), and 20 ml. of 2 M sodium hydroxide solution. The bottle was placed in a Parr shaker hydrogenator apparatus (Model No. 3911) then pressurized and vented alternately four times with hydrogen. On the fifth cycle the hydrogen pressure was adjusted to 50 psig, leak checked for 15 to 30 minutes, then agitation of the bottle was commenced at ambient temperature (about 25° C.). Pressure was recorded and maintained at 50 psig with time and when hydrogen uptake ceased in 3 hours the reaction bottle was vented and its contents recovered.

The reaction mixture was filtered over a bed of Celite filter aid to remove the catalyst. After separation of the two liquid layers, the organic phase was dried by storage over anhydrous sodium sulfate. The drying agent was removed by filtration and the filtrate rotary evaporated under about 15 mm. of mercury pressure and 40° C. to remove the toluene. Final traces of solvent were removed by heating the residue at about 40° C. under about 0.1 mm. of mercury for one hour to provide a final residual oil. Product analysis was carried out on the residue using C-13 nuclear magnetic resonance (NMR) spectroscopy with a Varian CFT 20 instrument and measuring the chemical shifts of the $\alpha$ and $\beta$ carbon atoms relative to the primary amine groups at 39.8 ppm. and 33.5 ppm. respectively as opposed to the chemical shifts of the $\alpha$ and $\beta$ carbon atoms due to the secondary amine by-product formation which appeared at 47.3 to 48.8 ppm. and 30.0 to 31.1 ppm. respectively. The conversion was 100 percent with a selectivity for the formation of 1,4-bis($\gamma$-aminopropoxy)butane at about 86.4 percent.

A comparison hydrogenation using the same procedure and ingredients in the proportions described above but in the absence of the 20 ml. of 2 M sodium hydroxide resulted in conversions of only 23 percent after 3 hours and 43 percent after 6 hours with final primary amine product of 1,4-bis($\gamma$-aminopropoxy)butane of only 28 percent and secondary amine by-product of 72 percent as measured by the NMR technique described above.

A second comparison hydrogenation was carried out identically to the above runs except that 20 ml. of plain water without the sodium hydroxide content was employed. Conversion was good at 100 percent after 4 hours; however, the selectivity was poor at only 40 percent of the desired 1,4-bis($\gamma$-aminopropoxy)butane.

EXAMPLE 2

The following experiment describes six reductions in accordance with the present invention (runs 1 to 6) and a reduction not so in accordance (run 7). The same general procedure was used in all the runs and is detailed as follows for run 1.

A 300 ml. stainless steel Parr autoclave reactor was equipped with a gas inlet valve, a gas release valve, and a stirring shaft with one turbine type impeller operating at 600 r.p.m. The reactor was also fitted with a stainless steel pressure gauge (0 to 2000 psig), an Inconel safety rupture disc rated for 1000 psig, and a Type J (iron constantan) thermocouple sealed in a stainless steel sheath which extended into the autoclave cavity. The reactor was heated by immersion in a silicone oil bath.

The autoclave was charged with 10 g. of a material obtained from the cyanoethylation of a polypropyleneoxy based triol having a molecular weight of about 3000. This material was analyzed by NMR to comprise about 77 percent of the cyanoethylated product. There was also charged 116 ml. (90 g.) of about 90 percent by weight based on substrate and organic solvent of cyclohexane, 396 mg. (about 2 mole percent rhodium per equivalent of nitrile) of 5 percent rhodium supported on carbon (Engelhard Lot 11953-27-D), and 47 ml. of 2 molar aqueous sodium hydroxide. The autoclave was flushed 5 times with hydrogen and pressurized to about 80 psig and heated to about 80° C. The hydrogen pressure was maintained at about 60 to 80 psig and when hydrogen uptake ceased (after about 3 hours), the hydrogenation was stopped.

The reaction solution was filtered over Celite filter aid to remove catalyst. The organic phase was separated from the aqueous phase, dried over anhydrous sodium sulfate, and the cyclohexane removed as described in Example 1 with a final drying of the residue under a vacuum of about 0.1 mm. of mercury pressure at 50° C. for about 0.5 hour. Thus, there was obtained 8.88 g. (88 percent yield) of a tri(γ-aminopropoxy) product as a dark viscous oil in accordance with this invention. As set forth in Table I below, NMR analysis showed no unreacted nitrile with a conversion of at least 95 percent and a selectivity of at least 95 percent to primary amine groups; amine eq. wt. observed = 1382. (Theory = 1057 assuming the starting material was 100 percent cyanoethylated.)

Runs 2 to 6 were carried out using essentially the same procedure and ingredients in the proportions described for run 1 above, except for the differences noted in Table I. The reduction in the caustic level to 5 ml. was without effect except where the concentration was lowered to 0.2 molar in run 2 which did lower the conversion. Cyclohexane and methylcyclohexane were interchangeable as solvents. The use of potassium and lithium hydroxide were less preferred than sodium hydroxide. The deletion of caustic in run 7 resulted in very little reduction occurring.

The deviations of the observed amine equivalents from theory and from each other reflect both the fact that the starting nitrile was only about 77 percent pure nitrile substrate and the products contained minor but varying proportions of secondary amine reduction products.

TABLE I

| Run | 1 | 2* | 3 | 4 | 5 | 6 | 7 |
|---|---|---|---|---|---|---|---|
| Base (ml.) | | | | | | | |
| NaOH | 47 | 5 | 5 | 5 | — | — | — |
| KOH | — | — | — | — | 5 | — | — |
| LiOH | — | — | — | — | — | 5 | — |
| Solvent (% by wt.) | | | | | | | |
| cyclohexane | 90 | — | — | 80 | — | — | — |
| methylcyclohexane | — | 90 | 90 | — | 90 | 90 | 90 |
| % Yield | 88 | 91 | 92 | — | 90 | 87 | 88** |
| % Conversion | >95 | 50 | >95 | >95 | >95 | >95 | 15 |
| % Selectivity (product) | >95 | 90 | >95 | 89 | 75 | 86 | — |
| Amine Eq. wt. Observed | 1382 | 1820 | 1472 | 1455 | 1471 | 1424 | — |

*The caustic solution used was 0.2 M instead of 2.0 M which was the concentration in all the other runs.
**Primarily recovery of starting nitrile.

EXAMPLE 3

The following experiment describes the hydrogenation (runs 8 to 13) of six different cyanoethylated polyols to their corresponding di- or tri(γ-aminopropoxy) derivatives in accordance with the present invention. The starting materials were the cyanoethylated products obtained from the cyanoethylation reactions of the six polyether polyols set forth in Table II using the well known methods for cyanoethylation reactions.

Run 8 was carried out in a 500 ml. glass reaction bottle using the Parr shaker apparatus described in Example 1, runs 9 to 11 and 13 were carried out using the 300 ml. autoclave described in Example 2 while run 12 was performed with the 600 ml. counterpart of the autoclave of Example 2. The various runs employed the ingredients set forth in Table II at the average temperatures and average hydrogen pressures shown along with the times for the respective hydrogenations. The reaction mixtures were worked up as in the previous examples by separating the organic layer from the aqueous phase, drying the solution and removing solvent to provide the residual clear to dark colored viscous oils. NMR analysis was again employed to determine the percent conversions and selectivity to the desired di- or tri(γ-aminopropoxy) derivatives. The yields of the individual products along with their conversions/selectivities are set forth in Table II along with the amine equivalent weights for the products of runs 9 and 11 to 13. It should be noted that the starting cyanoethylated polyols in runs 11 to 13 were only cyanoethylated to the respective levels of 50, 76, and 84 percent. Accordingly, the amine equivalent weights were skewed from their theoretical values not only by whatever minor secondary amine products were present but also by the lower levels of amine due to the lower proportions of cyanoethylated substrate. This is particularly noticeable in run 11 wherein the starting material contained only about 50 percent of cyanoethyl groups with the remainder being the unreacted polyol.

Reaction times in toluene were unnecessarily long due, primarily, to toluene absorbing the hydrogen. Solvents such as cyclohexane and methylcyclohexane resulted in times of only 2 to 3 hours for the reduction.

TABLE II

| Run | 8 | 9 | 10 | 11 | 12 | 13 |
|---|---|---|---|---|---|---|
| Cyanoethylated Polyol: grams (moles) | | | | | | |
| 400 MW polypropyleneoxy diol | 5.6 (0.0105) | — | — | — | — | — |
| 1000 MW polypropyleneoxy diol | — | 6.03 (0.0053) | — | — | — | — |
| 3000 MW polypropyleneoxy triol | — | — | 6.02 (0.002) | — | — | — |
| 5000 MW polypropyleneoxy triol[1] | — | — | — | 10.04 (0.002) | — | — |
| 2000 MW ethyleneoxy capped polypropyleneoxy diol[2] | — | — | — | — | 30.1 (0.014) | — |
| 6000 MW ethyleneoxy capped polypropyleneoxy triol[3] | — | — | — | — | — | 10.07 (0.0016) |
| 5% Rh/C (g.) | 1.02 | 0.424 | 0.257 | 0.240 | 0.888 | 0.207 |
| Solvent (% by wt.) | | | | | | |
| toluene | 95 | 90 | 93 | — | — | — |
| methylcyclohexane | — | — | — | 90 | — | 90 |
| cyclohexane | — | — | — | — | 90 | — |
| 2 M sodium hyroxide (ml.) | 40 | 40 | 40 | 47 | 15 | 5 |
| Temp. °C./Hydrogen psig | 25/40 | 75/37 | 80/37 | 65/78 | 79/94 | 72/84 |
| Time (hrs.) | 24 | 10 | 22 | 3.75 | 3 | 2 |
| % Conversion | >95 | >95 | >95 | >95 | >95 | >95 |
| % Selectivity (product) | 85 | 85 | 85 | >95 | 84 | 95 |
| Product yield (g.) | 5.2 | 5.0 | 6.6 | 8.9 | 27.8 | 10.1 |

TABLE II-continued

| Run | 8 | 9 | 10 | 11 | 12 | 13 |
|---|---|---|---|---|---|---|
| Amine Eq. Wt. | | | | | | |
| Observed | — | 666 | — | 3623 | 1345 | 2869 |
| Theory | — | 552 | — | 1718 | 1052 | 2052 |

Footnotes to Table II:
[1] Starting material only 50% capped with cyanoethyl groups.
[2] Starting material only 76% capped with cyanoethyl groups.
[3] Starting material only 84% capped with cyanoethyl groups.

I claim:

1. In a process for the catalytic hydrogenation of an organic nitrile group containing compound to a primary aminomethyl group in the presence of a rhodium catalyst, a basic substance, and a solvent, the improvement which comprises carrying out the reaction under a hydrogen pressure of from about 15 to 200 psig and employing a two-phase solvent system comprising an immiscible organic solvent selected from the group consisting of aromatic hydrocarbons, alicyclic hydrocarbons, alkanes, and mixtures thereof and water wherein said basic substance is present in from about 0.5 to about 5 molar concentration.

2. A process according to claim 1 wherein said immiscible solvent is an aromatic or alicyclic hydrocarbon.

3. A process according to claim 1 wherein said hydrogenation is carried out at a temperature of from about 20° to about 110° C.

4. A process according to claim 1 wherein said basic substance comprises a member selected from the group consisting of alkali metal hydroxides, alkali metal alkoxides, alkaline earth metal hydroxides, and quaternary ammonium hydroxides.

5. A process according to claim 1 wherein an organic compound having at least one aliphatic nitrile group is hydrogenated to the corresponding compound having at least one primary aminomethyl group.

6. A process for the catalytic hydrogenation of an organic compound having at least one aliphatic nitrile group to the corresponding compound having at least one primary aminomethyl group said process comprising hydrogenating said at least one aliphatic nitrile group under a hydrogen pressure of from about 15 to about 200 psig at a temperature of from about 20° to about 110° C. in the presence of (1) a supported rhodium catalyst; (2) a basic substance selected from the group consisting of alkali metal hydroxides, alkali metal alkoxides, alkaline earth metal hydroxides, and quaternary ammonium hydroxides; and (3) in a two-phase solvent system comprising an aqueous phase containing said basic substance in from about 0.5 to about 5 molar concentration and an immiscible organic solvent selected from the group consisting of aromatic hydrocarbons and alicyclic hydrocarbons.

7. A process according to claim 6 wherein said catalyst is employed in a range of from about 0.05 to about 30 mole percent of rhodium per equivalent of nitrile.

8. A process according to claim 6 wherein said basic substance is an alkali metal hydroxide.

9. A process according to claim 6 wherein said organic compound is present in a concentration of from about 2 to about 30 percent by weight in said organic phase.

10. A process according to claim 6 wherein an organic compound having from about 2 to about 4 $-OCH_2CH_2CN$ groups is hydrogenated to the corresponding di- to tetra-($\gamma$-aminopropoxy) compound in the presence of a 5 percent by weight rhodium on carbon catalyst in a two-phase solvent system comprising about a 2 molar solution of sodium hydroxide and an immiscible solvent selected from the group consisting of toluene, cyclohexane, and methylcyclohexane.

11. A process according to claim 10 wherein 1,4-bis($\beta$-cyanoethoxy)butane is hydrogenated to 1,4-bis($\gamma$-aminopropoxy)butane.

12. A process according to claim 10 wherein the di-cyanoethylated derivative of a polypropyleneoxy diol having a molecular weight of from about 300 to about 2000 is hydrogenated to the corresponding di($\gamma$-aminopropoxy) derivative.

13. A process according to claim 10 wherein the tri-cyanoethylated derivative of a polypropyleneoxy triol having a molecular weight of from about 2500 to about 6000 is hydrogenated to the corresponding tri($\gamma$-aminopropoxy) derivative.

14. A process according to claim 10 wherein the di-cyanoethylated derivative of an ethyleneoxy capped polypropyleneoxy diol having a molecular weight of from about 1500 to about 3000 is hydrogenated to the corresponding di($\gamma$-aminopropoxy) derivative.

15. A process according to claim 10 wherein the tri-cyanoethylated derivative of an ethyleneoxy capped polypropyleneoxy triol having a molecular weight of from about 5500 to about 6500 is hydrogenated to the corresponding tri($\gamma$-aminopropoxy) derivative.

* * * * *